(12) United States Patent
Strode et al.

(10) Patent No.: US 12,053,330 B2
(45) Date of Patent: Aug. 6, 2024

(54) SYSTEMS AND METHODS FOR TESTING MEMS ARRAYS AND ASSOCIATED ASICS

(71) Applicant: Exo Imaging, Inc., Redwood City, CA (US)

(72) Inventors: Jonathan Strode, Redwood City, CA (US); Rajeev Sivadasan, Redwood City, CA (US); Gordon Sasamori, Redwood City, CA (US)

(73) Assignee: Exo Imaging, Inc., Santa Clara, CA (US)

( * ) Notice: Subject to any disclaimer, the term of this patent is extended or adjusted under 35 U.S.C. 154(b) by 429 days.

(21) Appl. No.: 17/356,262

(22) Filed: Jun. 23, 2021

(65) Prior Publication Data

US 2022/0409184 A1  Dec. 29, 2022

(51) Int. Cl.
| | |
|---|---|
| *A61B 8/00* | (2006.01) |
| *B06B 1/02* | (2006.01) |
| *B06B 1/06* | (2006.01) |
| *G01S 15/89* | (2006.01) |

(52) U.S. Cl.
CPC .............. *A61B 8/58* (2013.01); *B06B 1/0207* (2013.01); *B06B 1/0292* (2013.01); *B06B 1/0622* (2013.01); *G01S 15/8915* (2013.01); *B06B 2201/40* (2013.01); *B06B 2201/51* (2013.01); *B06B 2201/55* (2013.01); *B06B 2201/76* (2013.01)

(58) Field of Classification Search
CPC ....... A61B 8/58; A61B 8/5207; A61B 8/4488; B06B 1/0207; B06B 1/0292; B06B 1/0622; B06B 1/0629; B06B 2201/40; B06B 2201/51; B06B 2201/55; B06B 2201/76; G01S 15/8915; G01S 7/5208; G01S 7/5205
See application file for complete search history.

(56) References Cited

U.S. PATENT DOCUMENTS

| | | | |
|---|---|---|---|
| 2,710,388 | A | 6/1955 | Chun |
| 3,100,886 | A | 8/1963 | Meyer et al. |
| 3,251,026 | A | 5/1966 | May, Jr. et al. |
| 3,980,905 | A | 9/1976 | Miller |
| 4,081,706 | A | 3/1978 | Edelson |
| 5,542,426 | A | 8/1996 | Watanabe et al. |
| 6,645,145 | B1 | 11/2003 | Dreschel et al. |

(Continued)

FOREIGN PATENT DOCUMENTS

| | | |
|---|---|---|
| CA | 2628100 C | 8/2016 |
| WO | WO-2020150253 A1 | 7/2020 |

OTHER PUBLICATIONS

Bjastad. High frame rate ultrasound imaging using parallel beamforming. Doctoral Thesis. Norwegian University of Science and Technology (136 pgs.) (Jan. 2009).

(Continued)

*Primary Examiner* — Suman K Nath
(74) *Attorney, Agent, or Firm* — Morgan, Lewis & Bockius LLP

(57) ABSTRACT

Described herein are methods and systems for testing transducers and associated integrated circuits. In some cases, a method or system described herein can comprise modulating a bias voltage using a test signal in order to produce a modulated bias voltage signal useful in testing a plurality of transducers of a transducer array in parallel.

20 Claims, 5 Drawing Sheets

(56) References Cited

U.S. PATENT DOCUMENTS

| | | | |
|---|---|---|---|
| 6,726,626 B1 | 4/2004 | Hossack | |
| 7,508,737 B1 | 3/2009 | Alexandru | |
| 7,824,335 B2 | 11/2010 | Wodnicki | |
| 7,901,358 B2 | 3/2011 | Mehi et al. | |
| 8,836,792 B1 | 9/2014 | Butler | |
| 11,058,396 B2 | 7/2021 | Haque et al. | |
| 2003/0036704 A1 | 2/2003 | Cerofolini | |
| 2003/0048698 A1* | 3/2003 | Barnes | H04R 23/00 367/181 |
| 2003/0149363 A1 | 8/2003 | Dreschel et al. | |
| 2004/0267134 A1 | 12/2004 | Hossack et al. | |
| 2005/0075572 A1 | 4/2005 | Mills et al. | |
| 2006/0052703 A1 | 3/2006 | Kumazawa | |
| 2008/0064959 A1 | 3/2008 | Kanda et al. | |
| 2009/0048522 A1 | 2/2009 | Huang | |
| 2009/0141592 A1 | 6/2009 | Huang | |
| 2009/0228229 A1 | 9/2009 | Trandafir | |
| 2009/0326609 A1 | 12/2009 | Doron | |
| 2010/0198070 A1 | 8/2010 | Asafusa et al. | |
| 2010/0242611 A1 | 9/2010 | Terazawa | |
| 2010/0244623 A1 | 9/2010 | Huang | |
| 2010/0312119 A1 | 12/2010 | Hashiba et al. | |
| 2011/0125022 A1 | 5/2011 | Lazebnik | |
| 2012/0068574 A1 | 3/2012 | Wu et al. | |
| 2012/0245457 A1 | 9/2012 | Crowley | |
| 2012/0316437 A1 | 12/2012 | Song et al. | |
| 2013/0334987 A1 | 12/2013 | Garg et al. | |
| 2013/0336095 A1 | 12/2013 | Seppa et al. | |
| 2014/0249414 A1 | 9/2014 | Herzog et al. | |
| 2015/0087991 A1 | 3/2015 | Chen et al. | |
| 2015/0265245 A1 | 9/2015 | Von Ramm et al. | |
| 2015/0374341 A1 | 12/2015 | Chen et al. | |
| 2016/0245894 A1 | 8/2016 | Deng et al. | |
| 2017/0117753 A1 | 4/2017 | Charthad et al. | |
| 2018/0028154 A1 | 2/2018 | Zhai | |
| 2018/0071775 A1 | 3/2018 | Zhuang et al. | |
| 2018/0153510 A1* | 6/2018 | Haque | G01S 7/52079 |
| 2018/0321381 A1 | 11/2018 | Cohen et al. | |
| 2019/0150881 A1 | 5/2019 | Maharbiz et al. | |
| 2019/0282834 A1 | 9/2019 | Zawada et al. | |
| 2019/0381535 A1 | 12/2019 | Zhuang et al. | |
| 2020/0221233 A1 | 7/2020 | Kent | |
| 2020/0346248 A1 | 11/2020 | Van Rens | |
| 2021/0293952 A1 | 9/2021 | Haque et al. | |

OTHER PUBLICATIONS

Lingvall. Time-domain Reconstruction Methods for Ultrasonic Array Imaging: A Statistical Approach. Doctoral Thesis Uppsala University Signals and Systems (193 pgs.) (2004).

PCT/US2020/013530 International Preliminary Report on Patentability dated Jul. 29, 2021.

PCT/US2020/013530 International Search Report and Written Opinion dated May 20, 2020.

PCT/US2020/013530 Invitation to Pay Additional Fees dated Mar. 16, 2020.

Rathod. A Review of Electric Impedance Matching Techniques for Piezoelectric Sensors, Actuators and Transducers. Electronics 8(2):169 (2019).

U.S. Appl. No. 17/156,058 Office Action dated Jun. 24, 2021.

PCT/US2021/038736 International Search Report and Written Opinion Oct. 20, 2021.

\* cited by examiner

SYSTEMS AND METHODS FOR TESTING MEMS ARRAYS AND ASSOCIATED ASICS

BACKGROUND

The present application relates to medical systems, methods, and systems, in particular for medical imaging such as with ultrasound.

Recently developed and commercialized ultrasound technologies have used arrays of MEMS (microelectromechanical systems) ultrasound transducers which can have numerous advantages over traditional piezoelectric transducers, for example, PZT transducers. Ultrasound MEMS arrays can comprise a large array of ultrasound transducers such as pMUTs (piezoelectric micromachined ultrasound transducers) and cMUTs (capacitive micromachined ultrasound transducers). These arrays are typically mounted on an ASIC (application specific integrated circuit), and in many cases, each ultrasound transducer needs to be tested to ensure that it is functional. Faults that can occur during manufacture can include: a MEMS device that has a broken membrane, a MEMS device that is short circuited or that has a weak or non-existent connection to the ASIC, among others. Testing of ultrasound MEMS arrays using existing technologies is complicated and time-consuming, for example, because current testing technologies require that the transducers be subjected to mechanical (e.g., ultrasound) stimulation in order to produce a testable output. Doing so can be both technically challenging and expensive in a test environment.

SUMMARY

Methods and systems disclosed herein drastically reduce the cost and complexity of testing ultrasound MEMS transducer arrays and associated ASICs. In some aspects, a method for testing a transducer array comprises: applying a test signal to a bias voltage signal to generate a modulated bias voltage signal; providing the modulated bias voltage signal to an ultrasound transducer array; measuring an output signal of the ultrasound transducer array; and determining whether the measured output signal is within a set of expected output limits. In some cases, the output signal is measured from a MEMS transducer or low-noise amplifier (LNA) of the ultrasound transducer array. In some cases, the method further comprises performing the measuring and determining for each MEMS transducer or LNA of a row of the ultrasound transducer array in parallel. In some cases, the method further comprises performing the measuring and determining for each row of the ultrasound transducer array in sequence. In some cases, the method further comprises performing the measuring and determining for each MEMS transducer or LNA of a column of the ultrasound transducer array in parallel. In some cases, the method further comprises performing the measuring and determining for each column of the ultrasound transducer array in sequence. In some cases, the method further comprises determining a total error number based on a total number of measured output signals that are determined not to be within the set of expected output limits. In some cases, the method further comprising identifying the ultrasound transducer array as rejected if the total error number exceeds an error count limit. In some cases, the set of expected output limits comprises an output voltage amplitude within 30% of an expected output voltage amplitude value. In some cases, the set of expected output limits comprises a signal frequency within 5% of an expected signal frequency value.

In various aspects, a system for testing a transducer array comprises: an ultrasound transducer array comprising a plurality of MEMS transducers; a bias voltage signal source; a test voltage signal source connected to the bias voltage signal source and the ultrasound transducer array in series; one or more controllers configured to perform the steps of: measuring an output signal of the ultrasound transducer array; and determining whether the measured output signal is within a set of expected output limits; a plurality of low-noise amplifiers (LNAs) connected in series with the ultrasound transducer array and the one or more controllers. In some cases, the output signal is measured from one or more of a MEMS transducer or LNA of the ultrasound transducer array. In some cases, the controller is configured to perform the measuring and determining for each MEMS and LNA of a row of the ultrasound transducer array in parallel. In some case, the controller is configured to perform the measuring and determining for each row of the ultrasound transducer array in sequence. In some cases, the controller is configured to perform the measuring and determining for each MEMS and LNA of a column of the ultrasound transducer array in parallel. In some cases, the controller is configured to perform the measuring and determining for each column of the ultrasound transducer array in sequence. In some cases, the controller is further configured to determine a total error number based on a total number of measured output signals that are determined not to be within the set of expected output limits. In some cases, the controller is further configured to identify the ultrasound transducer array as rejected if the total error number exceeds an error count limit. In some cases, the set of expected output limits comprises an output voltage amplitude within 30% of an expected output voltage amplitude value. In some cases, the set of expected output limits comprises a signal frequency within 5% of an expected signal frequency value.

BRIEF DESCRIPTION OF THE DRAWINGS

A better understanding of the features and advantages of the present subject matter will be obtained by reference to the following detailed description that sets forth illustrative embodiments, in which the principles of the invention are utilized, and the accompanying drawings of which.

DETAILED DESCRIPTION

Disclosed herein are methods and systems for improved testing of ultrasound transducer arrays. For example, methods and systems described herein comprise modulation of a bias voltage of an ultrasound transducer imager system or portion thereof can drastically reduce the time, cost, and technical difficulty of testing an ultrasound transducer array and application-specific integrated circuit (ASIC) of the ultrasound transducer imager. Modulating a bias voltage of an ultrasound transducer imager system can allow simultaneous interrogation of the connections and construction of a plurality of ultrasound imager system transducers (e.g., MEMS elements) and, in some cases, the application-specific integrated circuits (ASICs) associated with those transducers. In some cases, modulating the bias voltage allows interrogation of the connections and construction of an ultrasound imager's circuitry while avoiding the need to apply a precise mechanical input (e.g., using specialized testing equipment) to each transducer element (e.g., MEMS element) of the array (or tested portion thereof). Reductions in the time and complexity of testing ultrasound imager system components, e.g., as described herein, can significantly decrease the cost of production and can improve quality control.

Devices

Figure 1:
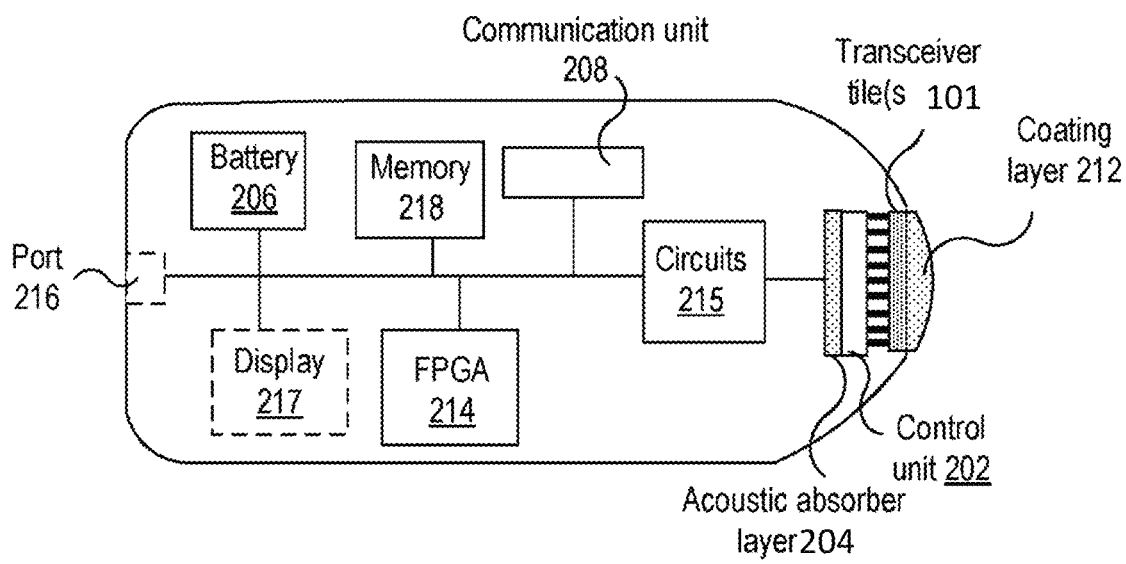
FIG. 1 shows a schematic diagram of a handheld ultrasound probe, according to embodiments.

In some cases (e.g., as shown in FIG. 1), an ultrasound imager system may include: a transducer array 101 (for example, comprising one or more transceiver tiles, which may each comprise a plurality of transducer elements), e.g., for transmitting and receiving pressure waves; a coating layer 212, which can operate as a lens for setting the propagation direction of and/or focusing the pressure waves and also functions as an acoustic impedance interface between the transceiver tile and the human body 110; a control unit 202, such as ASIC chip (or, shortly ASIC), for controlling the transceiver tile(s) 101; Field Programmable Gate Arrays (FPGAs) 214, e.g., for controlling the components of the ultrasound imager system; a circuit(s) 215, such as Analogue Front End (AFE), e.g., for processing/conditioning signals; an acoustic absorber layer 203, e.g., for absorbing waves generated by the transducer tiles 210, which may propagate toward the circuit 215; a communication unit 208, e.g., for communicating data with an external device wirelessly or through one or more ports 216; a memory 218, e.g., for storing data; a battery 206 for providing electrical power to the components of the imager; and, optionally, a display 217, e.g., for displaying images of target objects, such as internal organs of a patient.

Figure 2A:
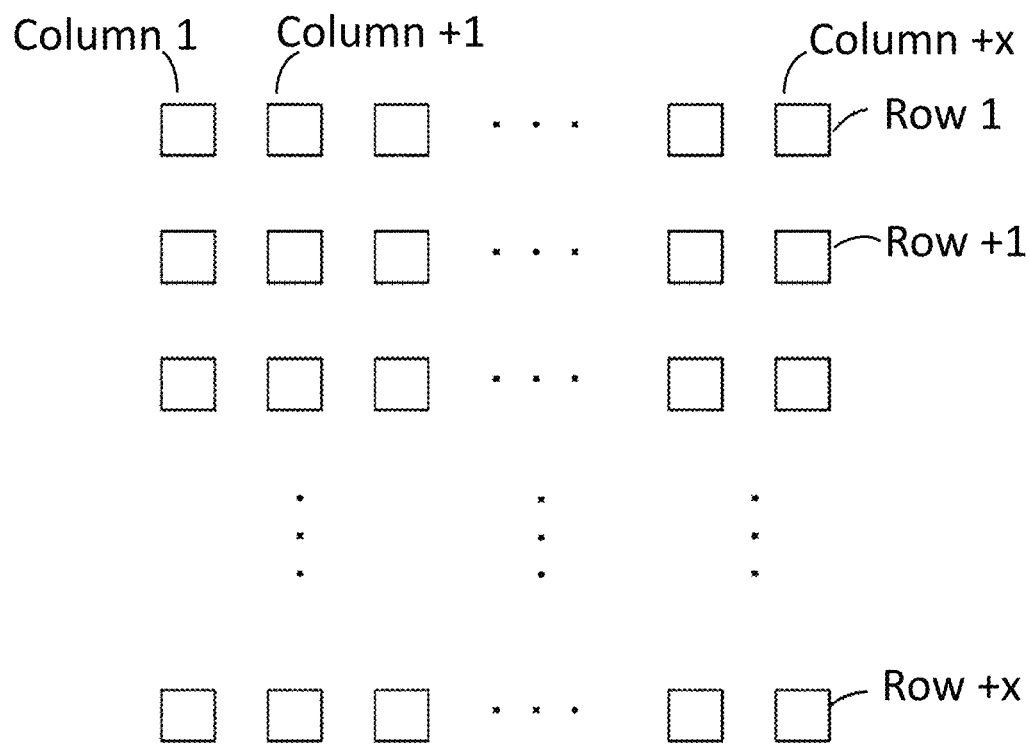
FIG. 2A shows a schematic diagram of a transducer array, according to embodiments.
Figure 2B:
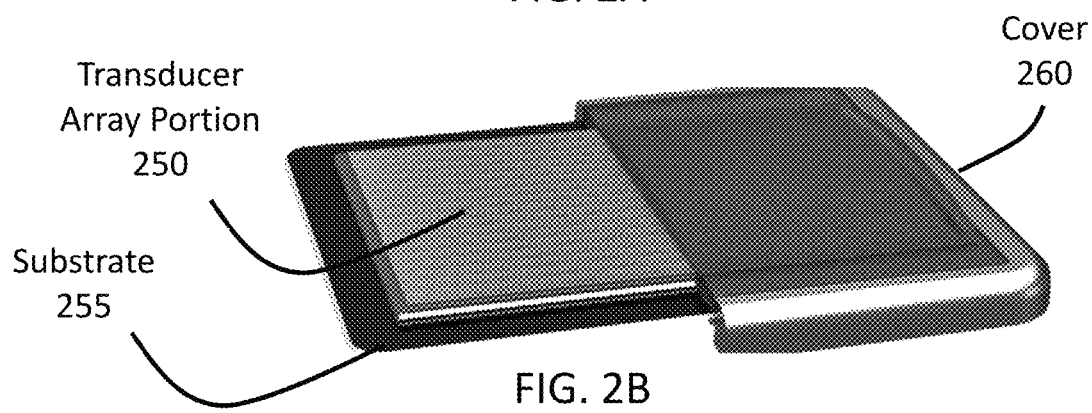
FIG. 2B shows a perspective view of a transducer array, according to embodiments.
Figure 2C:
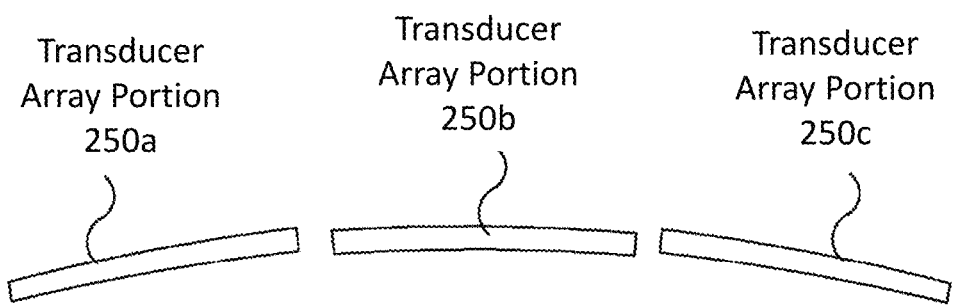
FIG. 2C shows a schematic diagram of a transducer array, according to embodiments.

In some cases, the plurality of transducer elements of an ultrasound transducer array can be spatially arranged into columns and rows (e.g., starting with column 1 and row 1, for example, as shown in FIG. 2A). In some cases, a plurality of transducers of an ultrasound transducer array portion 250 is arranged on a flat substrate 255 and a cover 260 may be provided (e.g., as shown in FIG. 2B). In some cases, a plurality of transducers of an ultrasound transducer array portion is arranged on a substrate that is curved (e.g., in cross-section), for example, as shown in FIG. 2C. In some cases, a plurality of transducer elements of an ultrasound transducer array can be divided into a plurality of transducer array portions 250a, 250b, 250c (e.g., as shown in FIG. 2C).

Transducer Arrays

Figure 3:
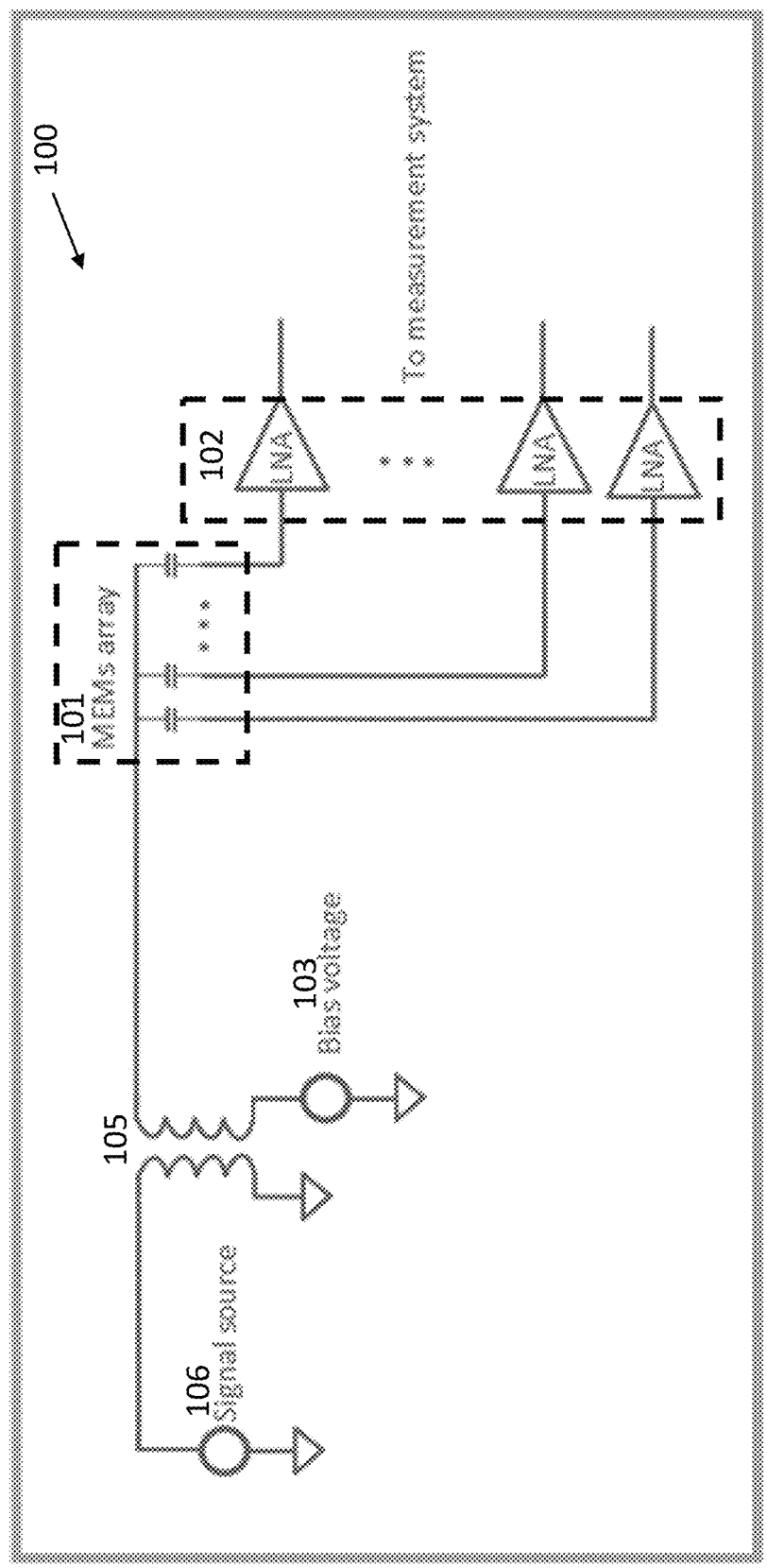
FIG. 3 shows a diagram of a testing circuit, according to embodiments

An ultrasound imager system (or an ultrasound imager test system 100) can comprise a transducer array 101, e.g., as illustrated in FIG. 3. An ultrasound transducer array or a portion thereof can comprise a plurality of micro-electro-mechanical system (MEMS) transducer elements (e.g, arranged in rows and columns on a substrate of the ultrasound imager system). In some cases, a MEMS transducer element can be a machined ultrasound transducer (MUT). In some cases, a machined ultrasound transducer (MUT) can be a piezoelectric micromachined ultrasound transducer (pMUT). In some cases, a micromachined ultrasound transducer (MUT) can be a capacitive micromachined ultrasound transducer (cMUT). An ultrasound imager system (or an ultrasound imager test system 100) can comprise a plurality of application-specific integrated circuit (ASIC) components 102. In some cases, a plurality of ASIC components 102 of an ultrasound imager system or ultrasound imager test system 100 can be coupled to a plurality of the transducer elements of the transducer array. ASIC components 102 of an ultrasound imager test system 100 can comprise one or more of low-noise amplifiers (LNA) (e.g., wherein an LNA is used to process signals from one or more transducers, for example, from a row of transducers). In some cases, one or more ASIC components 102 of an ultrasound imager system can used to control a plurality of the transducer elements of the transducer array. In some cases, one or more ASIC components 102 may be assembled as one unit together with the substrate and/or plurality of transducer elements. In some cases, one or more ASIC components 102 may be located outside of the ultrasound imager device and electrically coupled (e.g., via a cable) to the plurality of transducer elements.

An ultrasound imager system 100 can comprise a bias voltage source 103. A bias voltage can be a reference voltage (e.g., a static direct current (DC) voltage, such as a constant 0 V or a −18 V input signal) that can be used during testing and operation of an ultrasound array to normalize voltage modulation produced by the ultrasound transducer elements of an ultrasound transducer array, which can improve accuracy and precision of images produced by the array. A bias voltage can be distributed to each element of an ultrasound transducer array while in operation. Distribution of the bias voltage to each individual transducer array element (e.g., MEMS element) can facilitate the normalization of the output voltage of each individual transducer array element, which can be slightly different from one another (e.g., given the same input soundwave signal), for example, due to variability in transducer and/or ASIC construction associated with the manufacturing process.

As described herein, a bias voltage (e.g., produced by a bias voltage source 103) can be modulated, for example, with a test signal (e.g., generated by a test signal source 106). Modulation of a bias voltage with a test signal can result in a modulated bias voltage (e.g., comprising a superposition of the test signal and the bias voltage). In some cases, a transformer 105 (e.g., a step-down transformer) can be used to adjust (e.g., reduce) the amplitude of a test signal used to modulate a bias voltage (e.g., a constant bias voltage, such as a −18V bias voltage) of the ultrasound transducer imager), for example, as shown in FIG. 3. Transformer 105 can be connected in series with the bias voltage source 103.

In some cases, a test signal source 106 and a step-down transformer 105 used in testing can be external to the ultrasound transducer system or array. In some cases, the test signal source 106 and/or the step-down transformer 105 can be coupled to the ultrasound transducer imager between a bias voltage source 103 of the ultrasound transducer imager and an ultrasound transducer array 101 (e.g., a MEMS element array). Transducer elements of the transducer element array 101 can be coupled to a control circuit of the ultrasound imager (e.g., comprising an application specific integrated circuit (ASIC) 102, which can comprise a plurality of low-noise amplifiers and, in some cases, one or more bypass capacitors). Modulated bias voltage signals can be received after the ASIC circuit and can be analyzed for changes (e.g., with respect to amplitude, frequency, and/or waveform shape) to the expected modulated bias voltage signal, which may result from faults or defects in one or more of the MEMS transducer array and/or the ASIC of the ultrasound imager.

Modulation of the bias voltage (e.g., with a test signal, as described herein) can result in a more informative output signal (e.g., to be measured and/or processed by a measurement system 107) than an unmodulated bias voltage (or ASIC output signal utilizing an unmodulated bias voltage). For example, an injected test signal can have a defined waveform, which can be easily evaluated (e.g., using measurement system 107) for changes in amplitude, waveform shape, and/or changes to periodicity, e.g., that might result from defects in the hardware of the MEMS transducers of the transducer array and/or the ASIC of the ultrasound imager. In some cases, a test signal comprises a periodic waveform. For example, a test signal can have a sinusoidal waveform. In some cases, a test signal has a non-zero maximum amplitude. In some cases, a test signal can have a peak-to-peak amplitude (e.g., after step down transformer) of 0.1 millivolts to 3 millivolts. In some cases, a test signal can have a peak-to-peak amplitude (e.g., after step down transformer) of 0.1 millivolts to 0.3 millivolts, 0.1 millivolts to 0.5 millivolts, 0.1 millivolts to 1 millivolt, 0.1 millivolts to 2 millivolts, 0.1 millivolts to 2.5 millivolts, 0.1 millivolts to 3 millivolts, 0.3 millivolts to 0.5 millivolts, 0.3 millivolts to 1 millivolt, 0.3 millivolts to 2 millivolts, 0.3 millivolts to 2.5 millivolts, 0.3 millivolts to 3 millivolts, 0.5 millivolts to 1 millivolt, 0.5 millivolts to 2 millivolts, 0.5 millivolts to 2.5 millivolts, 0.5 millivolts to 3 millivolts, 1 millivolt to 2 millivolts, 1 millivolt to 2.5 millivolts, 1 millivolt to 3 millivolts, 2 millivolts to 2.5 millivolts, 2 millivolts to 3 millivolts, or 2.5 millivolts to 3 millivolts. In some cases, a test signal can have a peak-to-peak amplitude (e.g., after step down transformer) of 0.1 millivolts, 0.3 millivolts, 0.5 millivolts, 1 millivolt, 2 millivolts, 2.5 millivolts, or 3 millivolts. In some cases, a test signal can have a peak-to-peak amplitude (e.g., after step down transformer) of at least 0.1 millivolts, 0.3 millivolts, 0.5 millivolts, 1 millivolt, 2 millivolts, 2.5 millivolts, or 3 millivolts. In some cases, a test signal can have a peak-to-peak amplitude (e.g., after step down transformer) of at most 0.1 millivolts, 0.3 millivolts, 0.5 millivolts, 1 millivolt, 2 millivolts, 2.5 millivolts, or 3 millivolts.

Figure 4:
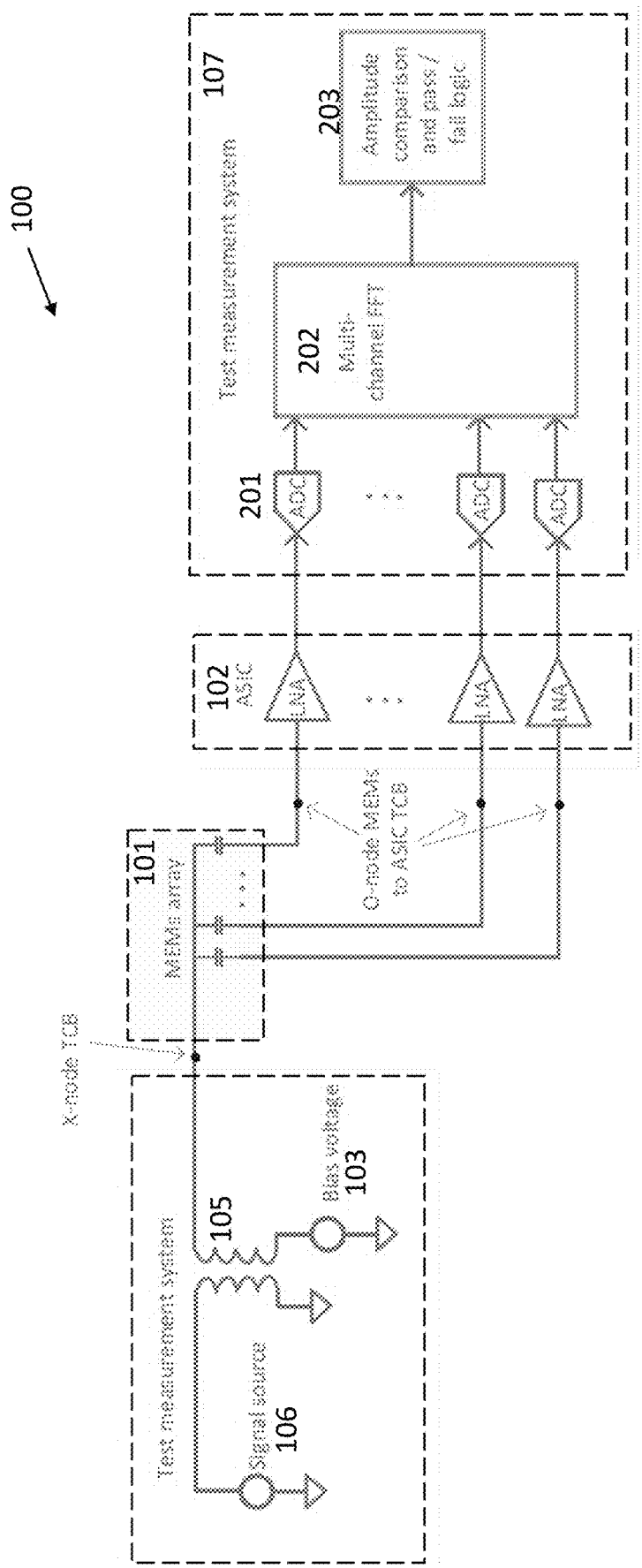
FIG. 4 shows a diagram of a testing circuit, according to embodiments.

In some cases, a fault or defect in an ultrasound transducer array (e.g., MEMS transducer array) or ASIC can be determined by the voltage or shape of a signal measured at a point in the ultrasound transducer system between the bias voltage source 103 (or transformer 105) and the transducer array 101 (e.g., at the MEMS bias node or at the X-node), between the transducer array 101 and the ASIC 102 (e.g., at the O-node or at the ASIC LNA input), and/or after the ASIC (e.g., at the ASIC LNA output), for example, as shown in FIG. 4. Table 1 shows some faults that can occur during manufacturing and effects that they can have on a modulated bias voltage signal, measured at various points in the circuit, assuming a −18 volt (V) constant bias voltage input and a 1 millivolt (mV) peak-to-peak alternating current (AC) test signal used to modulate the bias voltage. It is noted that the expected signal voltage at the ASIC LNA input under MEMS transducer element short circuit conditions shown in Table 1 (and denoted with a "*") is measured via voltage clamping using protection diodes. FIG. 4 shows a diagram of a test circuit with X-node and O-node reference points identified on the circuit.

TABLE 1

List of various expected signals for various fault conditions.

| Fault | MEMS bias node | ASIC LNA input | ASIC LNA output |
|---|---|---|---|
| No fault | $-18\,V_{DC} + 1m\,V_{AC}$ | $0\,V_{DC} + 1m\,V_{AC}$ | $30m\,V_{AC}$ |
| Failed O-node TCB bond | $-18\,V_{DC} + 1m\,V_{AC}$ | $0\,V_{DC}$ | $0\,V_{DC}$ |
| Failed X-node TCB bond | $0\,V_{DC}$ | $0\,V_{DC}$ | $0\,V_{DC}$ |
| Short circuit at MEMS | $-18\,V_{DC} + 1m\,V_{AC}$ | $-1.6\,V_{DC}$* | $0.9\,V_{DC}$ |
| Broken (open circuit) MEMS | $-18\,V_{DC} + 1m\,V_{AC}$ | $0\,V_{DC}$ | $0\,V_{DC}$ |
| Faulty LNA | $-18\,V_{DC} + 1m\,V_{AC}$ | $0\,V_{DC} + 1m\,V_{AC}$ | $<0.8 * 30m\,V_{AC}$ or $>1.2 * 30m\,V_{AC}$ |

As shown, an output signal measured after the LNAs of the ASIC can be measured as a 0 V constant signal for conditions such as a failed thermal compression bond (TCB) at the O-node or a broken MEMS transducer. A failure of the circuit before the bias voltage is introduced into the MEMS transducer array can also result in an output constant 0 V output signal after the ASIC LNAs; however, such a fault would also show a constant 0 V output signal at the MEMS bias node (e.g., A reduction or an increase of the amplitude of the output periodic signal can indicate a faulty ASIC component, such as a faulty LNA).

In some cases, a test measurement system 107 of an ultrasound imager test system 100 can comprise one or more analog-to-digital converters (ADC) 201. In some cases, signal output from each LNA of an ultrasound imager test system 100 is passed to a different ADC of a test measurement system 107. A controller 202 (e.g., comprising a processor and, optionally, a non-transitory memory) can be coupled to the one or more ADCs of a test measurement system 107. In some cases, one or more on-board ADCs of an ultrasound imager system can be utilized in testing the ultrasound imager system (e.g., wherein the ADCs of the ultrasound imager test system 100 comprise the on-board ADCs of the ultrasound imager system, for example, as opposed to utilizing ADCs of a separate test measurement system 107). In some cases, the controller 202 is configured to perform a fast Fourier transform (FFT) on data received from one or more LNAs. In some cases, the controller 202 comprises a multi-channel FFT system. In some cases, a test measurement system 107 comprises a signal analysis unit 203. In some cases, a signal analysis unit 203 comprises a processor (e.g., and a non-transitory memory) configured to perform one or more analyses on a signal received from one or more LNAs of the ultrasound imager system (e.g., via the ADC or controller of the test measurement system 107). In some cases, a signal analysis unit 203 is configured to perform signal amplitude comparison, waveform shape comparison, and/or pass/fail logic functions (e.g., on one or more signals received from the one or more LNAs of the ultrasound imager system).

In some cases, a test measurement system 107 can comprise a test signal source 106. In some cases, a test measurement system 107 can comprise a transformer 105. In some cases, a test measurement system 107 can comprise a bias voltage source 103.

In some cases, a test measurement system 107 or portion thereof is located local to the ASIC. In some cases, a test measurement system 107 or portion thereof is located remote from the ASIC (e.g., wherein the test measurement system 107 or portion thereof is coupled to the ASIC wirelessly or by a cable). In some cases, all or a portion of a test measurement system 107 (e.g., a test signal source 106, a transformer 105, one or more ADCs, one or more controllers, and/or one or more signal analysis units) can be removably coupled to a transducer array 101 and/or an ASIC 102 of an ultrasound transducer imager.

FIG. 4 shows an example of an ultrasound imager system 100. The signal source can be a low-impedance test signal source 106 (e.g., 50 ohms, 10 $V_{RMS}$), capable of producing a periodic test signal (e.g., a sinusoidal signal). A low-impedance (e.g., 0.35 ohm) step-down transformer (e.g., for reducing the peak-to-peak voltage of the test signal to +/−1 $mV_{RMS}$) can be placed in series with a bias voltage source (e.g., which may be used to supply a constant voltage bias input, for example of −18V). In some cases, a −18 $V_{DC}$+/−1 $mV_{RMS}$ signal can be measured at the input node of the MEMS transducer array 101 of the ultrasound transducer imager. In some cases, this MEMS input signal may be measured at the input node for the ASIC LNAs as a 1 $mV_{RMS}$ signal. In some cases, the signal can be measured at the ASIC LNA output node as a 30 $mV_{RMS}$ signal.

Methods of Testing MEMS Arrays and Associated ASIC

Figure 5:
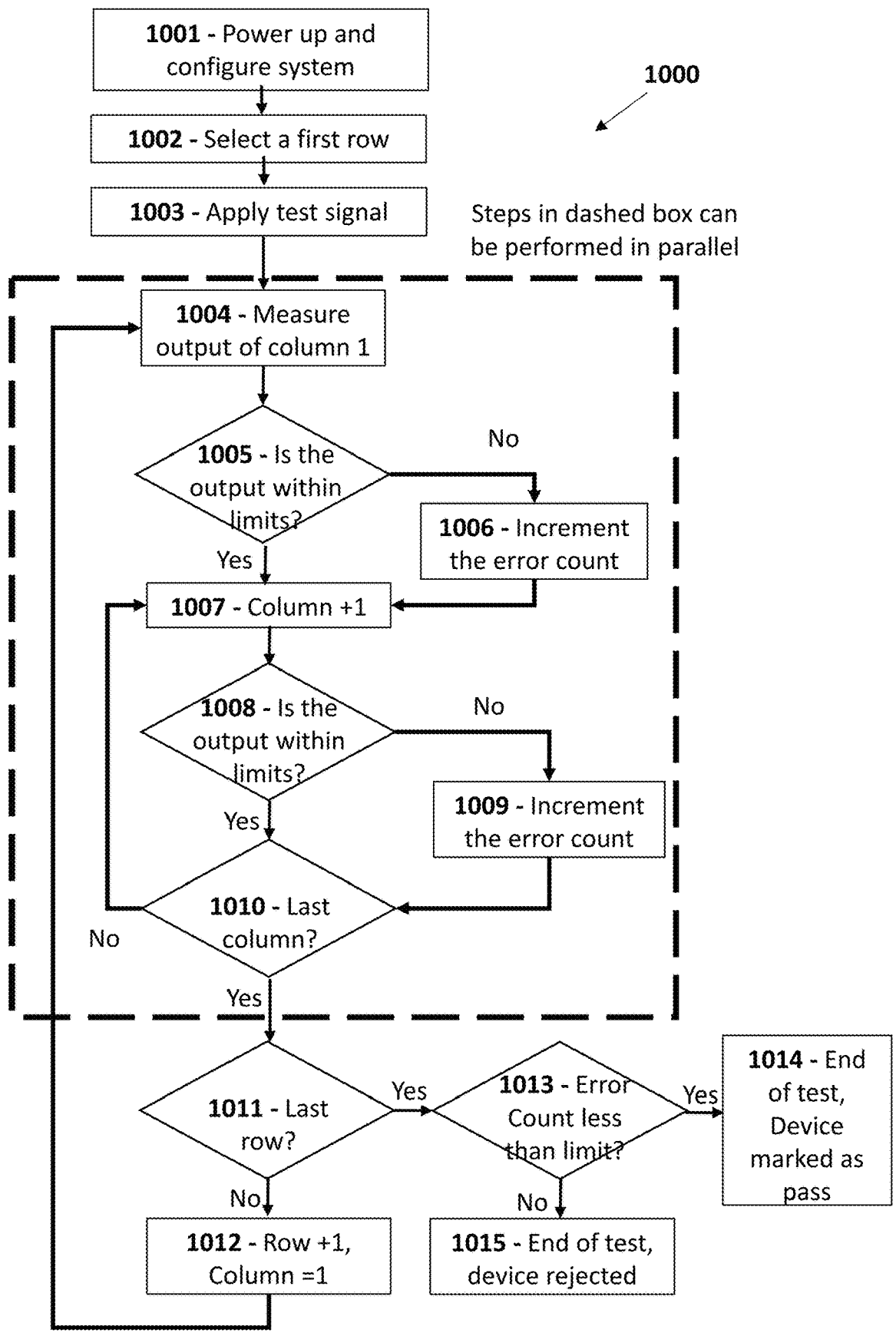
FIG. 5 shows a block diagram of testing processes, according to embodiments.

FIG. 5 shows steps of methods for testing a MEMS transducer array and associated ASIC. In some cases, the ASIC and MEMS array can be powered on and configured prior to testing (e.g., step 1001). This can comprise verification of baseline systems parameters, such as bias voltage parameters, and can involve connection of test signal source, transformer, and/or output signal measurement components. In some cases, a first row (e.g., row 1) of an ultrasound transducer array can be selected for testing prior to test signal introduction (e.g., step 1002). A first row may not necessarily be the topmost or leftmost row of transducers. In some cases, a first row is simply the first row tested, regardless of physical position on the array. In some cases, a first column is selected rather than a first row (e.g., in methods and systems where elements of each column are tested in parallel rather than elements of each row being tested in parallel, for example, as shown in FIG. 5).

As shown in step 1003 of FIG. 5, a test signal can be applied to the ultrasound imager system (e.g., using a test circuit, such as those shown in FIGS. 3-5). A test signal can be injected into the bias voltage for the MEMS using a transformer 105 (e.g., wherein the transformer 105 is placed in series with the bias voltage source 103). A test signal (e.g., for modulation of a bias voltage signal) can have a period waveform. In some cases, a sinusoidal test signal can be used. In selecting a test signal for use in methods and systems for testing an ultrasound transducer array 101 and/or ASIC 102, it can be advantageous to use a periodic signal with a frequency that is not excessively high or low. Attenuation of the periodic signal (e.g., due to capacitance on the transducer board) can be reduced or avoided by avoiding test signals with very high frequencies. In some cases, insufficiency of gain from the ASIC LNAs can be avoided if test signals with very low frequency are avoided. In some cases, a test signal can have a frequency of less than 5 kHz, 5 kHz to 10 kHz, 10 kHz to 15 kHz, 15 kHz to 20 kHz, 20 kHz to 25 kHz, 25 kHz to 30 kHz, 30 kHz to 35 kHz, 35 kHz to 40 kHz, 40 kHz to 45 kHz, 45 kHz to 50 kHz, or greater than 50 kHz. In some cases, a frequency in the range of 20 kHz (e.g., 15 kHz to 25 kHz) may be optimal.

In some cases, the test signal is injected into the bias voltage signal using a signal transformer 105 (e.g., a step-down signal transformer). In some cases, the use of a signal transformer has the advantage of reducing the source impedance, e.g., so that it can drive the large capacitive load. This test signal may be capacitively coupled to the input of the ASIC 102 by the MEMS capacitance.

As shown in step 1004, the output of the ASIC (e.g., for column 1) can be captured, for example, to detect faults in the MEMS array and/or the ASIC. In some cases, an output of an ultrasound MEMS array and ASIC system stimulated by a modulated bias signal (e.g., as described herein) can be evaluated as to whether it conforms to testing limits, for example, as shown in step 1005. In some cases, a measured signal that is not within expected (or required) output limits (e.g., with respect to amplitude, periodicity, phase, and/or frequency) can be classified as an error signal (e.g., which may result as a fault in the ultrasound imager system). In some cases, a damaged MEMS can have a significantly lower capacitance, which can result in a lower gain. In some cases, a damaged MEMS element can comprise a short circuit, which could cause the ASIC output to saturate. A failed bond between the ASIC and MEMS can result in the transducer circuit failing to produce an output. In some cases, the error count may be incremented (e.g., by one) and the measurement system can proceed to analyze the output from the next MEMS/ASIC (e.g., located in the next column, for example, column+1) if the measured signal is not within output limits (e.g., as shown in step 1006). If, instead, the measured signal is within output limits, the measurement system can proceed to analyze the output from the next MEMS/ASIC (e.g., located in the next column, for example, column+1), as shown in step 1007, without incrementing the error count. The output from the MEMS/ASIC located in the new column (e.g., column+1) can be analyzed for conformity with expected/required output limits (e.g., as shown in step 1008). Non-conformity with expected/required output limits may result in incrementation of the error count (e.g., by one), as shown in 1009. If the error count has been incremented or if the output was found to be within limits, a check may be performed (e.g., as shown in step 1010) to determine whether the previously tested MEMS/ASIC was in the last column of the array or portion thereof may be performed. In some cases, the test system can return to step 1007 and analyze the next MEMS/ASIC in the row if the previously analyzed MEMS/ASIC was not in the last column of the row/array. It is contemplated that steps 1004 to 1010 can be performed by progressing row-by-row instead of column-by-column, as shown in FIG. 5. In some cases, testing of each MEMS/ASIC element in a column (or row) of an ultrasound imager system (e.g., steps 1004 to 1010, as indicated by the dashed box in FIG. 5) can be performed in parallel. The MEMS can be tested in parallel, as the modified bias voltage signal can be applied to all MEMS at the same time.

If the MEMS/ASIC previously analyzed in steps 1008 to 1010 was located in the final column of the row (or final row of the column), a decision check can be performed (e.g., as shown in step 1011) to determine whether the analyzed row was the last row of the array (or whether the analyzed column the last column of the array). If the row (or column) was not the last in the array, the measurement system can proceed to analyze the output from the MEMS/ASIC in the first column of next row (e.g., row+1) (or, if proceeding down the rows of each column, the next column can be analyzed next), for example, as shown in step 1012, and the measurement system can perform analysis of the MEMS/ASIC elements in the next row (or column) for example in parallel.

If the decision check at step 1011 returns a result indicating that the previously analyzed MEMS/ASIC was the last row and column (e.g., row+x, column+x), a decision check can be made to determine whether the total error count is less than an allowable limit, for example, as shown in step 1013. If the error count is greater than or equal to (or alternatively greater than) the limit, the device/array may be marked as rejected (or "fail") and the test may be ended (e.g., as shown in step 1015). If the total error count is less than (or alternatively less than or equal to) the limit, the device/array may be marked as accepted (or "pass") and the test may be ended (e.g., as shown in step 1014). In some cases, an intermediate decision check may be performed at any step between step 1004 and 1013 to determine whether the total error count has been met or exceeded. In some cases, such an intermediate decision check may result in the device/array being marked as rejected (or "fail") and the test being ended if the total error count exceeds (or alternatively meets) the limit. If during such an intermediate decision check, it is found that the error count is less than (or alternatively equal to) the limit, the testing system may be allowed to continue to the testing method 1000.

Although the above steps show embodiments of methods of FIG. 5 to test a MEMS array transducer in accordance with embodiments, a person of ordinary still in the art will recognize many variations based on the teaching described herein. The steps may be completed in a different order. Steps may be added or deleted. Some of the steps may comprise sub-steps. Many of the steps may be repeated as often as advantageous to the testing.

One or more of the steps of the method of FIG. 5 may be performed with the circuitry as described herein, for example, using the ASIC described herein or other processing or logic circuitry. The circuitry may be programmed to provide one or more of the steps of the method of FIG. 5, and the program may comprise program instructions stored on a computer readable memory or programmed steps of the processing or logic circuitry, for example.

Error Conditions and Ultrasound System Faults

A method of testing an ultrasound transducer array (e.g., a MEMS array) or portion thereof can comprise identifying an error during testing. An error during testing can comprise a voltage, current, waveform, or portion of a waveform that deviates from an expected value or waveform shape. In some cases, an error identified, measured, or detected during testing can be the result of a fault in a MEMS array or portion thereof (e.g., a MEMS element or group of MEMS elements in the array). A method of testing a MEMS array or portion thereof can comprise identifying a fault in the MEMS array or a portion thereof (e.g., a MEMS element or group of MEMS elements of the array). In some cases, a lower number of faults in a MEMS array or portion thereof can result the MEMS array having higher sensitivity, higher accuracy, and/or more reproducible measurements, e.g., as compared to a MEMS array or portion thereof having a larger number of faults.

In some cases, an error can arise from a fault in a MEMS array or portion thereof. A fault can arise from a defect in the array or one or more connections to, from, or within the array. For example, a fault can arise from a damaged MEMS element, a short circuit, or a failed bond between the ASICs component and the MEMS component.

In some cases, identifying an error (e.g., as a result of a fault) in a MEMS array or portion thereof can comprise measuring an output of the MEMS array or portion thereof (e.g., in response to a test signal applied to the MEMS array or portion thereof). For example, an error (e.g., resulting from a system fault) can be identified in an ultrasound imager system or portion thereof (e.g., a MEMS element or group of MEMS elements of the array) by comparing the output of the ultrasound imager system (or ultrasound imager test system 100) or portion thereof to an expected output voltage value or expected output voltage range. In some cases, a method described herein can comprise determining whether an output signal of an ultrasound imager system (or ultrasound imager test system 100) is within a set of output limits. In some cases, the set of output limits comprises a range of expected output signal voltage amplitude values. In some cases, an expected output signal voltage amplitude value can be 0.1 volts to 1 volts, 0.1 volts to 2 volts, 0.1 volts to 3 volts, 0.1 volts to 4 volts, 0.1 volts to 5 volts, 0.1 volts to 7.5 volts, 0.1 volts to 10 volts, 0.1 volts to 15 volts, 0.1 volts to 18 volts, 0.1 volts to 20 volts, 1 volt to 2 volts, 1 volt to 3 volts, 1 volt to 4 volts, 1 volt to 5 volts, 1 volt to 7.5 volts, 1 volt to 10 volts, 1 volt to 15 volts, 1 volt to 18 volts, 1 volt to 20 volts, 2 volts to 3 volts, 2 volts to 4 volts, 2 volts to 5 volts, 2 volts to 7.5 volts, 2 volts to 10 volts, 2 volts to 15 volts, 2 volts to 18 volts, 2 volts to 20 volts, 3 volts to 4 volts, 3 volts to 5 volts, 3 volts to 7.5 volts, 3 volts to 10 volts, 3 volts to 15 volts, 3 volts to 18 volts, 3 volts to 20 volts, 4 volts to 5 volts, 4 volts to 7.5 volts, 4 volts to 10 volts, 4 volts to 15 volts, 4 volts to 18 volts, 4 volts to 20 volts, 5 volts to 7.5 volts, 5 volts to 10 volts, 5 volts to 15 volts, 5 volts to 18 volts, 5 volts to 20 volts, 7.5 volts to 10 volts, 7.5 volts to 15 volts, 7.5 volts to 18 volts, 7.5 volts to 20 volts, 10 volts to 15 volts, 10 volts to 18 volts, 10 volts to 20 volts, 15 volts to 18 volts, 15 volts to 20 volts, or 18 volts to 20 volts, or greater than 20 volts. In some cases, an expected output signal voltage amplitude value can be 0.1 volts, 1 volt, 2 volts, 3 volts, 4 volts, 5 volts, 7.5 volts, 10 volts, 15 volts, 18 volts, or 20 volts. In some cases, the set of output limits comprises a range of expected output signal frequency values. In some cases, an expected output signal frequency value can be 0.1 kHz to 1 kHz, 0.1 kHz to 5 kHz, 0.1 kHz to 10 kHz, 0.1 kHz to 15 kHz, 0.1 kHz to 20 kHz, 0.1 kHz to 25 kHz, 0.1 kHz to 30 kHz, 0.1 kHz to 35 kHz, 0.1 kHz to 40 kHz, 1 kHz to 5 kHz, 1 kHz to 10 kHz, 1 kHz to 15 kHz, 1 kHz to 20 kHz, 1 kHz to 25 kHz, 1 kHz to 30 kHz, 1 kHz to 35 kHz, 1 kHz to 40 kHz, 5 kHz to 10 kHz, 5 kHz to 15 kHz, 5 kHz to 20 kHz, 5 kHz to 25 kHz, 5 kHz to 30 kHz, 5 kHz to 35 kHz, 5 kHz to 40 kHz, 10 kHz to 15 kHz, 10 kHz to 20 kHz, 10 kHz to 25 kHz, 10 kHz to 30 kHz, 10 kHz to 35 kHz, 10 kHz to 40 kHz, 15 kHz to 20 kHz, 15 kHz to 25 kHz, 15 kHz to 30 kHz, 15 kHz to 35 kHz, 15 kHz to 40 kHz, 20 kHz to 25 kHz, 20 kHz to 30 kHz, 20 kHz to 35 kHz, 20 kHz to 40 kHz, 25 kHz to 30 kHz, 25 kHz to 35 kHz, 25 kHz to 40 kHz, 30 kHz to 35 kHz, 30 kHz to 40 kHz, or 35 kHz to 40 kHz, or greater than 40 kHz. In some cases, an expected output signal frequency value can be 0.1 kHz, 1 kHz, 5 kHz, 10 kHz, 15 kHz, 20 kHz, 25 kHz, 30 kHz, 35 kHz, or 40 kHz.

In some cases, an error may be determined to be present (or an error count may be increased by one) if a measured value (e.g., a measured output signal voltage amplitude and/or a measured output signal frequency can be 0.1% to 1%, 0.1% to 5%, 0.1% to 10%, 0.1% to 20%, 0.1% to 25%, 0.1% to 30%, 0.1% to 40%, 0.1% to 50%, 1% to 5%, 1% to 10%, 1% to 20%, 1% to 25%, 1% to 30%, 1% to 40%, 1% to 50%, 5% to 10%, 5% to 20%, 5% to 25%, 5% to 30%, 5% to 40%, 5% to 50%, 10% to 20%, 10% to 25%, 10% to 30%, 10% to 40%, 10% to 50%, 20% to 25%, 20% to 30%, 20% to 40%, 20% to 50%, 25% to 30%, 25% to 40%, 25% to 50%, 30% to 40%, 30% to 50%, or 40% to 50%, or greater than 50% greater than an expected value or range. In some cases, an error may be determined to be present (or an error count may be increased by one) if a measured value (e.g., a measured output signal voltage amplitude and/or a measured output signal frequency can be 0.1% to 1%, 0.1% to 5%, 0.1% to 10%, 0.1% to 20%, 0.1% to 25%, 0.1% to 30%, 0.1% to 40%, 0.1% to 50%, 1% to 5%, 1% to 10%, 1% to 20%, 1% to 25%, 1% to 30%, 1% to 40%, 1% to 50%, 5% to 10%, 5% to 20%, 5% to 25%, 5% to 30%, 5% to 40%, 5% to 50%, 10% to 20%, 10% to 25%, 10% to 30%, 10% to 40%, 10% to 50%, 20% to 25%, 20% to 30%, 20% to 40%, 20% to 50%, 25% to 30%, 25% to 40%, 25% to 50%, 30% to 40%, 30% to 50%, 40% to 50%, or greater than 50% less than an expected value or range.

Evaluation of a number of faults detected in a MEMS array or portion thereof, for example by summation of the total number of faults in the MEMS array or portion thereof, can be used to determine whether the MEMS array can be used or should be rejected. For example, a MEMS array in which the total number of faults detected exceeds a total fault limit or threshold value may be identified or marked as rejected, whereas a MEMS array in which the total number of faults detected in the array is less than or equal to the limit or threshold value may be identified or marked as acceptable (e.g., marked as "pass").

In some cases, a total fault limit or threshold can be determined based on an expected system performance parameter. In some cases, a total fault limit (e.g., pass/fail threshold value) can be determined based, at least in part, on a desired level of sensitivity, accuracy, and/or reproducibility of measurements. In some cases, a total fault limit (e.g., pass/fail threshold value) can be based, at least in part, on an expected number of faults a MEMS array or portion thereof may have before the desired level or performance is lost. In some cases, a total error limit (e.g., pass/fail threshold) can be 0.01 percent to 50 percent of MEMS elements per square millimeter. In some cases, a total error limit (e.g., pass/fail threshold) can be 0.01 percent to 0.1 percent, 0.01 percent to 1 percent, 0.01 percent to 2 percent, 0.01 percent to 3 percent, 0.01 percent to 4 percent, 0.01 percent to 5 percent, 0.01 percent to 7 percent, 0.01 percent to 10 percent, 0.01 percent to 20 percent, 0.01 percent to 25 percent, 0.01 percent to 50 percent, 0.1 percent to 1 percent, 0.1 percent to 2 percent, 0.1 percent to 3 percent, 0.1 percent to 4 percent, 0.1 percent to 5 percent, 0.1 percent to 7 percent, 0.1 percent to 10 percent, 0.1 percent to 20 percent, 0.1 percent to 25 percent, 0.1 percent to 50 percent, 1 percent to 2 percent, 1 percent to 3 percent, 1 percent to 4 percent, 1 percent to 5 percent, 1 percent to 7 percent, 1 percent to 10 percent, 1 percent to 20 percent, 1 percent to 25 percent, 1 percent to 50 percent, 2 percent to 3 percent, 2 percent to 4 percent, 2 percent to 5 percent, 2 percent to 7 percent, 2 percent to 10 percent, 2 percent to 20 percent, 2 percent to 25 percent, 2 percent to 50 percent, 3 percent to 4 percent, 3 percent to 5 percent, 3 percent to 7 percent, 3 percent to 10 percent, 3 percent to 20 percent, 3 percent to 25 percent, 3 percent to 50 percent, 4 percent to 5 percent, 4 percent to 7 percent, 4 percent to 10 percent, 4 percent to 20 percent, 4 percent to 25 percent, 4 percent to 50 percent, 5 percent to 7 percent, 5 percent to 10 percent, 5 percent to 20 percent, 5 percent to 25 percent, 5 percent to 50 percent, 7 percent to 10 percent, 7 percent to 20 percent, 7 percent to 25 percent, 7 percent to 50 percent, 10 percent to 20 percent, 10 percent to 25 percent, 10 percent to 50 percent, 20 percent to 25 percent, 20 percent to 50 percent, or 25 percent to 50 percent of MEMS elements per square millimeter. In some cases, a total error limit (e.g., pass/fail threshold) can be 0.01 percent, 0.1 percent, 1 percent, 2 percent, 3 percent, 4 percent, 5 percent, 7 percent, 10 percent, 20 percent, 25 percent, or 50 percent of MEMS elements per square millimeter. In some cases, a total error limit (e.g., pass/fail threshold) can be at least 0.01 percent, 0.1 percent, 1 percent, 2 percent, 3 percent, 4 percent, 5 percent, 7 percent, 10 percent, 20 percent, 25 percent, or 50 percent. In some cases, a total error limit (e.g., pass/fail threshold) can be at most 0.01 percent, 0.1 percent, 1 percent, 2 percent, 3 percent, 4 percent, 5 percent, 7 percent, 10 percent, 20 percent, 25 percent, or 50 percent of MEMS elements per square millimeter.

In some cases, a total error limit (e.g., pass/fail threshold value) can be based, at least in part, on the distribution of total faults per MEMS array or portion thereof across a production batch of MEMS arrays. For example, pass/fail determinations can be made based on an analysis of MEMS arrays from a production run binned by total fault number. In some embodiments, only the top quintile, top two quintiles, top three quintiles, top four quintiles, top quartile, top two quartiles, top three quartiles, top third, top two thirds, or top half of tested MEMS arrays (e.g., ranked or binned by total number of faults per array, faults per MEMS element, or errors per square millimeter of array area) is identified or marked as "pass" (e.g., identified or marked as useable and/or subsequently incorporated into a final device for sale).

Methods and systems for testing ultrasound devices and portions thereof (e.g., MEMS arrays or portions thereof, ASICs, etc.) can significantly reduce the time (and cost) of producing and testing ultrasound device components (e.g., MEMS arrays, portions of MEMS arrays, ASICs, etc.), for example, compared to current production and testing methods and systems, which can require using a probe to provide mechanical signals individual transducer elements sequentially. Advantageously, methods and systems described herein can utilize the bias voltage (e.g., modulated as described herein) to test device components in parallel without necessitating the mechanical modulation of a deformable transducer element. In some cases, methods and systems can be used to test a plurality of elements in parallel. For example, a testing system or method described herein can be configured to test 1, 2, 3, 4, 5, 6, 7, 8, 9, 10, 10 to 20, 20 to 30, 30 to 40, 40 to 50, 50 to 100, 100 to 200, 200 to 500, 500 to 1000, or greater than 1000 MEMS elements in parallel. In some cases, elements of an ultrasound transducer array can be tested according in order of their arrangement on the substrate. For example, all or a portion of the MEMS elements in a row of an array (e.g., as shown in FIG. 2A) or a column of an array can be tested in parallel. In some cases, a row or column of MEMS elements can be tested in 20 microseconds to 50,000 microseconds. In some cases, a row or column of MEMS elements can be tested in 20 microseconds to 50 microseconds, 20 microseconds to 100 microseconds, 20 microseconds to 150 microseconds, 20 microseconds to 200 microseconds, 20 microseconds to 500 microseconds, 20 microseconds to 1,000 microseconds, 20 microseconds to 5,000 microseconds, 20 microseconds to 10,000 microseconds, 20 microseconds to 50,000 microseconds, 50 microseconds to 100 microseconds, 50 microseconds to 150 microseconds, 50 microseconds to 200 microseconds, 50 microseconds to 500 microseconds, 50 microseconds to 1,000 microseconds, 50 microseconds to 5,000 microseconds, 50 microseconds to 10,000 microseconds, 50 microseconds to 50,000 microseconds, 100 microseconds to 150 microseconds, 100 microseconds to 200 microseconds, 100 microseconds to 500 microseconds, 100 microseconds to 1,000 microseconds, 100 microseconds to 5,000 microseconds, 100 microseconds to 10,000 microseconds, 100 microseconds to 50,000 microseconds, 150 microseconds to 200 microseconds, 150 microseconds to 500 microseconds, 150 microseconds to 1,000 microseconds, 150 microseconds to 5,000 microseconds, 150 microseconds to 10,000 microseconds, 150 microseconds to 50,000 microseconds, 200 microseconds to 500 microseconds, 200 microseconds to 1,000 microseconds, 200 microseconds to 5,000 microseconds, 200 microseconds to 10,000 microseconds, 200 microseconds to 50,000 microseconds, 500 microseconds to 1,000 microseconds, 500 microseconds to 5,000 microseconds, 500 microseconds to 10,000 microseconds, 500 microseconds to 50,000 microseconds, 1,000 microseconds to 5,000 microseconds, 1,000 microseconds to 10,000 microseconds, 1,000 microseconds to 50,000 microseconds, 5,000 microseconds to 10,000 microseconds, 5,000 microseconds to 50,000 microseconds, or 10,000 microseconds to 50,000 microseconds. In some cases, a row or column of MEMS elements can be tested in 20 microseconds, 50 microseconds, 100 microseconds, 150 microseconds, 200 microseconds, 500 microseconds, 1,000 microseconds, 5,000 microseconds, 10,000 microseconds, or 50,000 microseconds. In some cases, a row or column of MEMS elements can be tested in at least 20 microseconds, 50 microseconds, 100 microseconds, 150 microseconds, 200 microseconds, 500 microseconds, 1,000 microseconds, 5,000 microseconds, 10,000 microseconds, or 50,000 microseconds. In some cases, a row or column of MEMS elements can be tested in at most 20 microseconds, 50 microseconds, 100 microseconds, 150 microseconds, 200 microseconds, 500 microseconds, 1,000 microseconds, 5,000 microseconds, 10,000 microseconds, or 50,000 microseconds. In some cases, a row or column of MEMS elements can be tested in 0.05 seconds to 0.10 seconds. In some cases, a row or column of MEMS elements can be tested in 0.1 seconds to 100 seconds. In some cases, a row or column of MEMS elements can be tested in 0.1 seconds to 0.2 seconds, 0.1 seconds to 0.5 seconds, 0.1 seconds to 1 second, 0.1 seconds to 2 seconds, 0.1 seconds to 3 seconds, 0.1 seconds to 4 seconds, 0.1 seconds to 5 seconds, 0.1 seconds to 10 seconds, 0.1 seconds to 100 seconds, 0.2 seconds to 0.5 seconds, 0.2 seconds to 1 second, 0.2 seconds to 2 seconds, 0.2 seconds to 3 seconds, 0.2 seconds to 4 seconds, 0.2 seconds to 5 seconds, 0.2 seconds to 10 seconds, 0.2 seconds to 100 seconds, 0.5 seconds to 1 second, 0.5 seconds to 2 seconds, 0.5 seconds to 3 seconds, 0.5 seconds to 4 seconds, 0.5 seconds to 5 seconds, 0.5 seconds to 10 seconds, 0.5 seconds to 100 seconds, 1 second to 2 seconds, 1 second to 3 seconds, 1 second to 4 seconds, 1 second to 5 seconds, 1 second to 10 seconds, 1 second to 100 seconds, 2 seconds to 3 seconds, 2 seconds to 4 seconds, 2 seconds to 5 seconds, 2 seconds to 10 seconds, 2 seconds to 100 seconds, 3 seconds to 4 seconds, 3 seconds to 5 seconds, 3 seconds to 10 seconds, 3 seconds to 100 seconds, 4 seconds to 5 seconds, 4 seconds to 10 seconds, 4 seconds to 100 seconds, 5 seconds to 10 seconds, 5 seconds to 100 seconds, or 10 seconds to 100 seconds. In some cases, a row or column of MEMS elements can be tested in 0.1 seconds, 0.2 seconds, 0.5 seconds, 1 second, 2 seconds, 3 seconds, 4 seconds, 5 seconds, 10 seconds, or 100 seconds. In some cases, a row or column of MEMS elements can be tested in at least 0.1 seconds, 0.2 seconds, 0.5 seconds, 1 second, 2 seconds, 3 seconds, 4 seconds, 5 seconds, 10 seconds, or 100 seconds. In some cases, a row or column of MEMS elements can be tested in at most 0.1 seconds, 0.2 seconds, 0.5 seconds, 1 second, 2 seconds, 3 seconds, 4 seconds, 5 seconds, 10 seconds, or 100 seconds.

In some cases, a row or column of an ultrasound array or portion thereof can have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 35 to 40, 40 to 50, 50 to 100, 100 to 200, 200 to 500, or more than 500 MEMS elements.

In some cases, a MEMS ultrasound array can be tested in 0.01 milliseconds to 50 milliseconds. In some cases, a MEMS ultrasound array can be tested in 0.01 milliseconds to 0.1 milliseconds, 0.01 milliseconds to 1 millisecond, 0.01 milliseconds to 2 milliseconds, 0.01 milliseconds to 3 milliseconds, 0.01 milliseconds to 3.5 milliseconds, 0.01 milliseconds to 4 milliseconds, 0.01 milliseconds to 5 milliseconds, 0.01 milliseconds to 7.5 milliseconds, 0.01 milliseconds to 10 milliseconds, 0.01 milliseconds to 20 milliseconds, 0.01 milliseconds to 50 milliseconds, 0.1 milliseconds to 1 millisecond, 0.1 milliseconds to 2 milliseconds, 0.1 milliseconds to 3 milliseconds, 0.1 milliseconds to 3.5 milliseconds, 0.1 milliseconds to 4 milliseconds, 0.1 milliseconds to 5 milliseconds, 0.1 milliseconds to 7.5 milliseconds, 0.1 milliseconds to 10 milliseconds, 0.1 milliseconds to 20 milliseconds, 0.1 milliseconds to 50 milliseconds, 1 millisecond to 2 milliseconds, 1 millisecond to 3 milliseconds, 1 millisecond to 3.5 milliseconds, 1 millisecond to 4 milliseconds, 1 millisecond to 5 milliseconds, 1 millisecond to 7.5 milliseconds, 1 millisecond to 10 milliseconds, 1 millisecond to 20 milliseconds, 1 millisecond to 50 milliseconds, 2 milliseconds to 3 milliseconds, 2 milliseconds to 3.5 milliseconds, 2 milliseconds to 4 milliseconds, 2 milliseconds to 5 milliseconds, 2 milliseconds to 7.5 milliseconds, 2 milliseconds to 10 milliseconds, 2 milliseconds to 20 milliseconds, 2 milliseconds to 50 milliseconds, 3 milliseconds to 3.5 milliseconds, 3 milliseconds to 4 milliseconds, 3 milliseconds to 5 milliseconds, 3 milliseconds to 7.5 milliseconds, 3 milliseconds to 10 milliseconds, 3 milliseconds to 20 milliseconds, 3 milliseconds to 50 milliseconds, 3.5 milliseconds to 4 milliseconds, 3.5 milliseconds to 5 milliseconds, 3.5 milliseconds to 7.5 milliseconds, 3.5 milliseconds to 10 milliseconds, 3.5 milliseconds to 20 milliseconds, 3.5 milliseconds to 50 milliseconds, 4 milliseconds to 5 milliseconds, 4 milliseconds to 7.5 milliseconds, 4 milliseconds to 10 milliseconds, 4 milliseconds to 20 milliseconds, 4 milliseconds to 50 milliseconds, 5 milliseconds to 7.5 milliseconds, 5 milliseconds to 10 milliseconds, 5 milliseconds to 20 milliseconds, 5 milliseconds to 50 milliseconds, 7.5 milliseconds to 10 milliseconds, 7.5 milliseconds to 20 milliseconds, 7.5 milliseconds to 50 milliseconds, 10 milliseconds to 20 milliseconds, 10 milliseconds to 50 milliseconds, or 20 milliseconds to 50 milliseconds. In some cases, a MEMS ultrasound array can be tested in 0.01 milliseconds, 0.1 milliseconds, 1 millisecond, 2 milliseconds, 3 milliseconds, 3.5 milliseconds, 4 milliseconds, 5 milliseconds, 7.5 milliseconds, 10 milliseconds, 20 milliseconds, or 50 milliseconds. In some cases, a MEMS ultrasound array can be tested in at least 0.01 milliseconds, 0.1 milliseconds, 1 millisecond, 2 milliseconds, 3 milliseconds, 3.5 milliseconds, 4 milliseconds, 5 milliseconds, 7.5 milliseconds, 10 milliseconds, 20 milliseconds, or 50 milliseconds. In some cases, a MEMS ultrasound array can be tested in at most 0.01 milliseconds, 0.1 milliseconds, 1 millisecond, 2 milliseconds, 3 milliseconds, 3.5 milliseconds, 4 milliseconds, 5 milliseconds, 7.5 milliseconds, 10 milliseconds, 20 milliseconds, or 50 milliseconds.

In some cases, methods and systems for testing MEMS arrays or a portion thereof described herein can reduce the time required to test an ultrasound array by at least 5%, at least 10%, at least 15%, at least 20%, at least 25%, at least 30%, at least 35%, at least 40%, at least 45%, at least 50%, 1% to 5%, 5% to 10%, 10% to 20%, 20% to 30%, 30% to 40%, 40% to 50%, or more than 50%, e.g., compared to mechanical testing (e.g., using a test ultrasound wave).

Unless otherwise defined, all technical terms used herein have the same meaning as commonly understood by one of ordinary skill in the art to which this subject matter belongs.

Although certain embodiments and examples are provided in the foregoing description, the inventive subject matter extends beyond the specifically disclosed embodiments to other alternative embodiments and/or uses, and to modifications and equivalents thereof. Thus, the scope of the claims appended hereto is not limited by any of the particular embodiments described herein. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not necessarily be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

As used herein A and/or B encompasses one or more of A or B, and combinations thereof such as A and B. It will be understood that although the terms "first," "second," "third," etc. may be used herein to describe various elements, components, regions and/or sections, these elements, components, regions and/or sections should not necessarily be limited by these terms. These terms may be used merely to distinguish one element, component, region or section from another element, component, region, or section. Thus, a first element, component, region or section discussed herein could be termed a second element, component, region or section without departing from the teachings of the present disclosure, in some cases.

As used herein, the singular forms "a," "an," and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence of addition of one or more other features, regions, integers, steps, operations, elements, components, and/or groups thereof. As used herein, the term "and/or" includes any and all combinations of one or more of the associated listed items.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise As used in this specification and the claims, unless otherwise stated, the term "about," and "approximately," or "substantially" refers to variations of less than or equal to +/−0.1%, +/−1%, +/−2%, +/−3%, +/−4%, +/−5%, +/−6%, +/−7%, +/−8%, +/−9%, +/−10%, +/−11%, +/−12%, +/−14%, +/−15%, or +/−20%, including increments therein, of the numerical value depending on the embodiment. As a non-limiting example, about 100 meters represents a range of 95 meters to 105 meters (which is +/−5% of 100 meters), 90 to 110 meters (which is +/−10% of 100 meters), or 85 meters to 115 meters (which is +/−15% of 100 meters) depending on the embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for testing a transducer array, the method comprising:
    applying a test signal to a bias voltage signal to generate a modulated bias voltage signal;
    providing the modulated bias voltage signal to an ultrasound transducer array;
    measuring an output voltage signal of the ultrasound transducer array; and
    determining whether the measured output voltage signal is within a set of expected output limits.

2. The method of claim 1, wherein the output voltage signal is measured from a MEMS transducer or low-noise amplifier (LNA) of the ultrasound transducer array.

3. The method of claim 2, further comprising performing the measuring and determining for each MEMS transducer or LNA of a row of the ultrasound transducer array in parallel.

4. The method of claim 3, further comprising performing the measuring and determining for each row of the ultrasound transducer array in sequence.

5. The method of claim 2, further comprising performing the measuring and determining for each MEMS transducer or LNA of a column of the ultrasound transducer array in parallel.

6. The method of claim 5, further comprising performing the measuring and determining for each column of the ultrasound transducer array in sequence.

7. The method of claim 1, further comprising determining a total error number based on a total number of measured output signals that are determined not to be within the set of expected output limits and identifying the ultrasound transducer array as rejected if the total error number exceeds an error count limit.

8. The method of claim 1, wherein the set of expected output limits comprises an output voltage amplitude within 30% of an expected output voltage amplitude value.

9. The method of claim 1, wherein the set of expected output limits comprises a signal frequency within 5% of an expected signal frequency value.

10. The method of claim 1, wherein the providing the modulated bias voltage signal provides a non-mechanical stimulation of the array.

11. The method of claim 1, wherein the providing the modulated bias voltage signal comprises providing a voltage via direct electrical connection with the ultrasound transducer array.

12. A system for testing a transducer array, the system comprising:
- an ultrasound transducer array comprising a plurality of MEMS transducers;
- a bias voltage signal source;
- a test voltage signal source connected to the bias voltage signal source and the ultrasound transducer array in series;
- one or more controllers configured to perform the steps of:
  - measuring an output voltage signal of the ultrasound transducer array; and
  - determining whether the measured output voltage signal is within a set of expected output limits;
- a plurality of low-noise amplifiers (LNAs) connected in series with the ultrasound transducer array and the one or more controllers.

13. The system of claim 12, wherein the output voltage signal is measured from one or more of a MEMS transducer or LNA of the ultrasound transducer array.

14. The system of claim 13, wherein the controller is configured to perform the measuring and determining for each MEMS or LNA of a row of the ultrasound transducer array in parallel.

15. The system of claim 14, wherein the controller is configured to perform the measuring and determining for each row of the ultrasound transducer array in sequence.

16. The system of claim 13, wherein the controller is configured to perform the measuring and determining for each MEMS or LNA of a column of the ultrasound transducer array in parallel.

17. The system of claim 16, wherein the controller is configured to perform the measuring and determining for each column of the ultrasound transducer array in sequence.

18. The system of claim 12, wherein the controller is further configured to determine a total error number based on a total number of measured output signals that are determined not to be within the set of expected output limits, and wherein the controller is further configured to identify the ultrasound transducer array as rejected if the total error number exceeds an error count limit.

19. The system of claim 12, wherein the set of expected output limits comprises an output voltage amplitude within 30% of an expected output voltage amplitude value.

20. The system of claim 12, wherein the set of expected output limits comprises a signal frequency within 5% of an expected signal frequency value.

* * * * *